(12) United States Patent
Han

(10) Patent No.: US 10,568,528 B2
(45) Date of Patent: Feb. 25, 2020

(54) BLOOD PRESSURE DETECTION METHOD AND SPHYGMOMANOMETER

(71) Applicant: BOE TECHNOLOGY GROUP CO., LTD., Beijing (CN)

(72) Inventor: Yang Han, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 200 days.

(21) Appl. No.: 15/675,016

(22) Filed: Aug. 11, 2017

(65) Prior Publication Data

US 2018/0110426 A1 Apr. 26, 2018

(30) Foreign Application Priority Data

Oct. 20, 2016 (CN) .......................... 2016 1 0916421

(51) Int. Cl.
*A61B 5/02* (2006.01)
*A61B 5/021* (2006.01)
(Continued)

(52) U.S. Cl.
CPC .......... *A61B 5/02141* (2013.01); *A61B 5/022* (2013.01); *A61B 5/02108* (2013.01);
(Continued)

(58) Field of Classification Search
CPC .......... A61B 5/02141; A61B 5/020108; A61B 5/02133; A61B 5/022; A61B 8/04; A61B 8/488
(Continued)

(56) References Cited

U.S. PATENT DOCUMENTS 3,527,197 A 9/1970 Ware et al.
3,532,085 A 10/1970 Massie et al.
(Continued)

FOREIGN PATENT DOCUMENTS

| CN | 101548883 A | 10/2009 |
| CN | 103610454 A | 3/2014 |
| WO | 2013005179 A1 | 1/2013 |

OTHER PUBLICATIONS

First Office Action for Chinese Application No. 201610916421.8, dated Jul. 4, 2017, 6 pages.
(Continued)

*Primary Examiner* — Tarun Sinha
(74) *Attorney, Agent, or Firm* — Brooks Kushman P.C.

(57) ABSTRACT

A blood pressure detection method is used for the sphygmomanometer including an envelope, an air pressure control mechanism, an ultrasonic wave transmission mechanism and an ultrasonic wave reception mechanism. The blood pressure detection method includes: applying a control signal to the air pressure control mechanism and the ultrasonic wave transmission mechanism, to inflate and deflate the envelope, and enable the ultrasonic wave transmission mechanism to transmit an ultrasonic detection signal toward the to-be-detected body part at a predetermined interval; monitoring an ultrasonic reflection signal received by the ultrasonic wave reception mechanism; determining a detection time point for the blood pressure detection in accordance with a frequency of the ultrasonic reflection signal during the deflation of the envelope; and determining a blood pressure value for the blood pressure detection in accordance with a pressure value of air within the envelope at the detection time point.

20 Claims, 4 Drawing Sheets

(51) Int. Cl.
  *A61B 5/022*   (2006.01)
  *A61B 8/08*    (2006.01)
  *A61B 8/04*    (2006.01)
  *A61B 5/0225*   (2006.01)
  *A61B 5/024*   (2006.01)

(52) U.S. Cl.
  CPC ............ *A61B 5/02133* (2013.01); *A61B 8/04* (2013.01); *A61B 8/488* (2013.01); *A61B 5/0225* (2013.01); *A61B 5/02427* (2013.01)

(58) Field of Classification Search
  USPC .......................................................... 73/602
  See application file for complete search history.

(56) References Cited

U.S. PATENT DOCUMENTS

| | | |
|---|---|---|
| 3,663,932 A | 5/1972 | Mount et al. |
| 2014/0148702 A1 | 5/2014 | Chen |

OTHER PUBLICATIONS

Second Office Action for Chinese Application No. 201610916421.8, dated Oct. 16, 2017, 5 pages.
Chinese Search Report for Application No. 201610916421.8, dated Apr. 27, 2017, 7 pages.

S110 — applying a control signal to the air pressure control mechanism and the ultrasonic wave transmission mechanism, to enable the air pressure control mechanism to initiate an air pressure operation on the envelope in accordance with the received control signal, thereby to inflate and deflate the envelope sequentially, and enable the ultrasonic wave transmission mechanism to initiate the transmission of an ultrasonic detection signal in accordance with the received control signal, thereby to transmit the ultrasonic detection signal toward the to-be-detected body part at a predetermined interval

S120 — monitoring an ultrasonic reflection signal received by the ultrasonic wave reception mechanism

S130 — determining a detection time point for the blood pressure detection in accordance with a frequency of the ultrasonic reflection signal during the deflation of the envelope

S140 — determining a blood pressure value for the blood pressure detection in accordance with a pressure value of air within the envelope at the detection time point

Fig. 1

S131 — during the deflation of an envelope, monitoring a difference between a frequency of the ultrasonic reflection signal and a frequency of the ultrasonic detection signal within each time period

S132 — comparing a difference between the frequency of the ultrasonic reflection signal and the frequency of the ultrasonic detection signal within a current time period with a difference between a frequency of the ultrasonic reflection signal and the frequency of the ultrasonic detection signal within each of the predetermined number of previous time periods previous to the current time period, so as to determine the detection time point for the blood pressure detection

Fig. 2

BLOOD PRESSURE DETECTION METHOD AND SPHYGMOMANOMETER

CROSS-REFERENCE TO RELATED APPLICATION

The present application claims a priority of the Chinese patent application No. 201610916421.8 filed on Oct. 20, 2016, which is incorporated herein by reference in its entirety.

TECHNICAL FIELD

The present disclosure relates to the field of medical measurement technology, in particular to a blood pressure detection method and a sphygmomanometer.

BACKGROUND

Along with the increase of incidence of hypertension, a sphygmomanometer has become an indispensable household appliance for the early detection of hypertension and the monitoring of a therapeutic effect. Currently, a commonly-used method for measuring a blood pressure mainly includes increasing pressure through inflation and reducing pressure through deflation, so as to monitor blood flow in an upper arm and determine a systolic pressure and a diastolic pressure, thereby to perform the blood pressure detection.

In order to prevent a detection result from being adversely affected by the movement of the arm, during the detection, it is necessary to ensure the arm is at rest, so the application of the above-mentioned detection method is limited.

SUMMARY

An object of the present disclosure is to provide a blood pressure detection method and a sphygmomanometer, so as to prevent a detection result from being adversely affected during the detection by the blood pressure detection method in the related art due to the movement of the arm.

In one aspect, the present disclosure provides in some embodiments a blood pressure detection method for a sphygmomanometer including an envelope for covering a to-be-detected body part during the blood pressure detection, an air pressure control mechanism configured to inflate and deflate the envelope, and an ultrasonic wave transmission mechanism and an ultrasonic wave reception mechanism arranged on the envelope. The blood pressure detection method includes steps of: applying a control signal to the air pressure control mechanism and the ultrasonic wave transmission mechanism, to enable the air pressure control mechanism to initiate an air pressure operation on the envelope in accordance with the received control signal, thereby to inflate and deflate the envelope sequentially, and enable the ultrasonic wave transmission mechanism to initiate the transmission of an ultrasonic detection signal in accordance with the received control signal, thereby to transmit the ultrasonic detection signal toward the to-be-detected body part at a predetermined interval; monitoring an ultrasonic reflection signal received by the ultrasonic wave reception mechanism; determining a detection time point for the blood pressure detection in accordance with a frequency of the ultrasonic reflection signal during the deflation of the envelope; and determining a blood pressure value for the blood pressure detection in accordance with a pressure value of air within the envelope at the detection time point.

In a possible embodiment of the present disclosure, in the above blood pressure detection method, the step of determining the detection time point for the blood pressure detection in accordance with the frequency of the ultrasonic reflection signal during the deflation of the envelope includes: during the deflation of the envelope, monitoring a difference between a frequency of the ultrasonic reflection signal and a frequency of the ultrasonic detection signal within each time period; and comparing a difference between the frequency of the ultrasonic reflection signal and the frequency of the ultrasonic detection signal within a current time period with a difference between a frequency of the ultrasonic reflection signal and the frequency of the ultrasonic detection signal within each of the predetermined number of previous time periods previous to the current time period, so as to determine the detection time point for the blood pressure detection.

In a possible embodiment of the present disclosure, in the above blood pressure detection method, the step of comparing the difference between the frequency of the ultrasonic reflection signal and the frequency of the ultrasonic detection signal within the current time period with the difference between the frequency of the ultrasonic reflection signal and the frequency of the ultrasonic detection signal within each of the predetermined number of previous time periods so as to determine the detection time point for the blood pressure detection includes: in the case that an absolute value of the difference between the frequency of the ultrasonic reflection signal and the frequency of the ultrasonic detection signal within the current time period is greater than or equal to a first predetermined value, and an absolute value of the difference between the frequency of the ultrasonic reflection signal and the frequency of the ultrasonic detection signal within each of the predetermined number of previous time periods previous to the current time period is smaller than or equal to a second predetermined value, determining a reception time point for the ultrasonic reflection signal within the current time period as a detection time point for the detection of a systolic pressure; and in the case that the absolute value of the difference between the frequency of the ultrasonic reflection signal and the frequency of the ultrasonic detection signal within the current time period is smaller than or equal to the second predetermined value, and the absolute value of the difference between the frequency of the ultrasonic reflection signal and the frequency of the ultrasonic detection signal within each of the predetermined number of previous time periods previous to the current time period is greater than or equal to a third predetermined value, determining a reception time point for the ultrasonic reflection signal within the current time period as a detection time point for the detection of a diastolic pressure. The first predetermined value is greater than or equal to the third predetermined value, and the third predetermined value is greater than or equal to the second predetermined value.

In a possible embodiment of the present disclosure, in the above blood pressure detection method, the step of determining the blood pressure value for the blood pressure detection in accordance with the pressure value of the air within the envelope at the detection time point includes: detecting a pressure value outputted by the air pressure control mechanism at the detection time point; and setting the pressure value outputted by the air pressure control mechanism at the detection time point as the pressure value of the air within the envelope, and setting the pressure value of the air within the envelope as the blood pressure value.

In a possible embodiment of the present disclosure, in the above blood pressure detection method, subsequent to the step of monitoring the ultrasonic reflection signal received by the ultrasonic wave reception mechanism, the blood pressure detection method further includes: determining a switching time point for switching from an inflation procedure to a deflation procedure in accordance with the frequency of the ultrasonic reflection signal during the inflation of the envelope, and transmitting a switching signal for switching from the inflation procedure to the deflation procedure to the air pressure control mechanism; and determining an end time point for the deflation procedure in accordance with the frequency of the ultrasonic reflection signal during the deflation of the envelope, and transmitting a deflation end signal to the air pressure control mechanism.

In a possible embodiment of the present disclosure, in the above blood pressure detection method, the step of determining the switching time point for switching from the inflation procedure to the deflation procedure in accordance with the frequency of the ultrasonic reflection signal during the inflation of the envelope includes: during the inflation of the envelope, monitoring a difference between the frequency of the ultrasonic reflection signal and the frequency of the ultrasonic detection signal within each time period; and in the case that an absolute value of a difference between the frequency of the ultrasonic reflection signal and the frequency of the ultrasonic detection signal within a current time period is smaller than or equal to a fourth predetermined value, and an absolute value of a difference between the frequency of the ultrasonic reflection signal and the frequency of the ultrasonic detection signal within each of the predetermined number of previous time periods previous to the current time period is greater than the fourth predetermined value, determining a reception time point for the ultrasonic reflection signal within the current time period as the switching time point for switching from the inflation procedure to the deflation procedure. The step of determining the end time point for the deflation procedure in accordance with the frequency of the ultrasonic reflection signal during the deflation of the envelope includes: during the deflation of the envelope, monitoring a difference between a frequency of the ultrasonic reflection signal and the frequency of the ultrasonic detection signal within each time period; and in the case that an absolute value of a difference between the frequency of the ultrasonic reflection signal and the frequency of the ultrasonic detection signal within the current time period is smaller than or equal to the fourth predetermined value, and an absolute value of a difference between the frequency of the ultrasonic reflection signal and the frequency of the ultrasonic detection signal within each of the predetermined number of previous time periods previous to the current time period is greater than the fourth predetermined value, determining a reception time point for the ultrasonic reflection signal within the current time period as the end time point for the deflation procedure.

In a possible embodiment of the present disclosure, in the above blood pressure detection method, the step of monitoring the difference between the frequency of the ultrasonic reflection signal and the frequency of the ultrasonic detection signal within each time period includes: acquiring a first frequency of the ultrasonic detection signal transmitted by the ultrasonic wave transmission mechanism at a start time point of each time period; acquiring a second frequency of the ultrasonic reflection signal received by the ultrasonic wave reception mechanism at an end time point of each time period; and calculating the difference in accordance with the second frequency and the first frequency.

In another aspect, the present disclosure provides in some embodiments a sphygmomanometer including an envelope for covering a to-be-detected body part during the blood pressure detection, an air pressure control mechanism configured to inflate and deflate the envelope, and an ultrasonic wave transmission mechanism and an ultrasonic wave reception mechanism arranged on the envelope. The sphygmomanometer further includes: a signal output circuit configured to apply a control signal to the air pressure control mechanism and the ultrasonic wave transmission mechanism, to enable the air pressure control mechanism to initiate an air pressure operation on the envelope in accordance with the received control signal, thereby to inflate and deflate the envelope sequentially, and enable the ultrasonic wave transmission mechanism to initiate the transmission of an ultrasonic detection signal in accordance with the received control signal, thereby to transmit the ultrasonic detection signal toward the to-be-detected body part at a predetermined interval; a signal detection circuit configured to monitor an ultrasonic reflection signal received by the ultrasonic wave reception mechanism; a first analyzing circuit configured to determine a detection time point for the blood pressure detection in accordance with a frequency of the ultrasonic reflection signal during the deflation of the envelope; and a second analyzing circuit configured to determine a blood pressure value for the blood pressure detection in accordance with a pressure value of air within the envelope at the detection time point.

In a possible embodiment of the present disclosure, in the sphygmomanometer, the first analyzing circuit includes: a frequency detection circuit configured to, during the deflation of the envelope, monitor a difference between a frequency of the ultrasonic reflection signal and a frequency of the ultrasonic detection signal within each time period; and a first calculation circuit configured to compare a difference between the frequency of the ultrasonic reflection signal and the frequency of the ultrasonic detection signal within a current time period with a difference between a frequency of the ultrasonic reflection signal and the frequency of the ultrasonic detection signal within each of the predetermined number of previous time periods previous to the current time period, so as to determine the detection time point for the blood pressure detection.

In a possible embodiment of the present disclosure, in the sphygmomanometer, the first calculation circuit is further configured to: in the case that an absolute value of the difference between the frequency of the ultrasonic reflection signal and the frequency of the ultrasonic detection signal within the current time period is greater than or equal to a first predetermined value, and an absolute value of the difference between the frequency of the ultrasonic reflection signal and the frequency of the ultrasonic detection signal within each of the predetermined number of previous time periods previous to the current time period is smaller than or equal to a second predetermined value, determine a reception time point for the ultrasonic reflection signal within the current time period as a detection time point for the detection of a systolic pressure; and in the case that the absolute value of the difference between the frequency of the ultrasonic reflection signal and the frequency of the ultrasonic detection signal within the current time period is smaller than or equal to the second predetermined value, and the absolute value of the difference between the frequency of the ultrasonic reflection signal and the frequency of the ultrasonic detection signal within each of the predetermined number of previous time periods previous to the current time period is greater than or equal to a third predetermined value, determine a reception time point for the ultrasonic reflection signal within the current time period as a detection time point for the detection of a diastolic pressure. The first predetermined value is greater than or equal to the third predetermined value, and the third predetermined value is greater than or equal to the second predetermined value.

In a possible embodiment of the present disclosure, in the sphygmomanometer, the second analyzing circuit includes: a pressure detection circuit configured to detect a pressure value outputted by the air pressure control mechanism at the detection time point; and a pressure setting circuit configured to set the pressure value outputted by the air pressure control mechanism at the detection time point as the pressure value of the air within the envelope, and set the pressure value of the air within the envelope as the blood pressure value.

In a possible embodiment of the present disclosure, the sphygmomanometer further includes: a third analyzing circuit configured to determine a switching time point for switching from an inflation procedure to a deflation procedure in accordance with the frequency of the ultrasonic reflection signal during the inflation of the envelope, and transmit a switching signal for switching from the inflation procedure to the deflation procedure to the air pressure control mechanism; and a fourth analyzing circuit configured to determine an end time point for the deflation procedure in accordance with the frequency of the ultrasonic reflection signal during the deflation of the envelope, and transmit a deflation end signal to the air pressure control mechanism.

In a possible embodiment of the present disclosure, in the sphygmomanometer, the third analyzing circuit includes: a frequency detection circuit configured to, during the inflation of the envelope, monitor a difference between the frequency of the ultrasonic reflection signal and the frequency of the ultrasonic detection signal within each time period; and a second calculation circuit configured to, in the case that an absolute value of a difference between the frequency of the ultrasonic reflection signal and the frequency of the ultrasonic detection signal within a current time period is smaller than or equal to a fourth predetermined value, and an absolute value of a difference between the frequency of the ultrasonic reflection signal and the frequency of the ultrasonic detection signal within each of the predetermined number of previous time periods previous to the current time period is greater than the fourth predetermined value, determine a reception time point for the ultrasonic reflection signal within the current time period as the switching time point for switching from the inflation procedure to the deflation procedure. The fourth analyzing circuit includes: a frequency detection circuit configured to, during the deflation of the envelope, monitor a difference between a frequency of the ultrasonic reflection signal and the frequency of the ultrasonic detection signal within each time period; and a third calculation circuit configured to, in the case that an absolute value of a difference between the frequency of the ultrasonic reflection signal and the frequency of the ultrasonic detection signal within the current time period is smaller than or equal to the fourth predetermined value, and an absolute value of a difference between the frequency of the ultrasonic reflection signal and the frequency of the ultrasonic detection signal within each of the predetermined number of previous time periods previous to the current time period is greater than the fourth predetermined value, determine a reception time point for the ultrasonic reflection signal within the current time period as the end time point for the deflation procedure.

In a possible embodiment of the present disclosure, in the sphygmomanometer, the frequency detection circuit includes: a first frequency acquisition circuit configured to acquire a first frequency of the ultrasonic detection signal transmitted by the ultrasonic wave transmission mechanism at a start time point of each time period; a second frequency acquisition circuit configured to acquire a second frequency of the ultrasonic reflection signal received by the ultrasonic wave reception mechanism at an end time point of each time period; and a difference calculation circuit configured to calculate the difference in accordance with the second frequency and the first frequency.

In a possible embodiment of the present disclosure, in the sphygmomanometer, the envelope is of a size matching a size of a finger or toe of a human body.

BRIEF DESCRIPTION OF THE DRAWINGS

In order to illustrate the technical solutions of the present disclosure in a clearer manner, the drawings desired for the present disclosure will be described hereinafter briefly. Obviously, the following drawings merely relate to some embodiments of the present disclosure, and based on these drawings, a person skilled in the art may obtain the other drawings without any creative effort.

FIG. 1 is a flow chart of a blood pressure detection method according to some embodiments of the present disclosure;

FIG. 2 is a flow chart of Step S130 in FIG. 1;

DETAILED DESCRIPTION OF THE EMBODIMENTS

Figure 3:
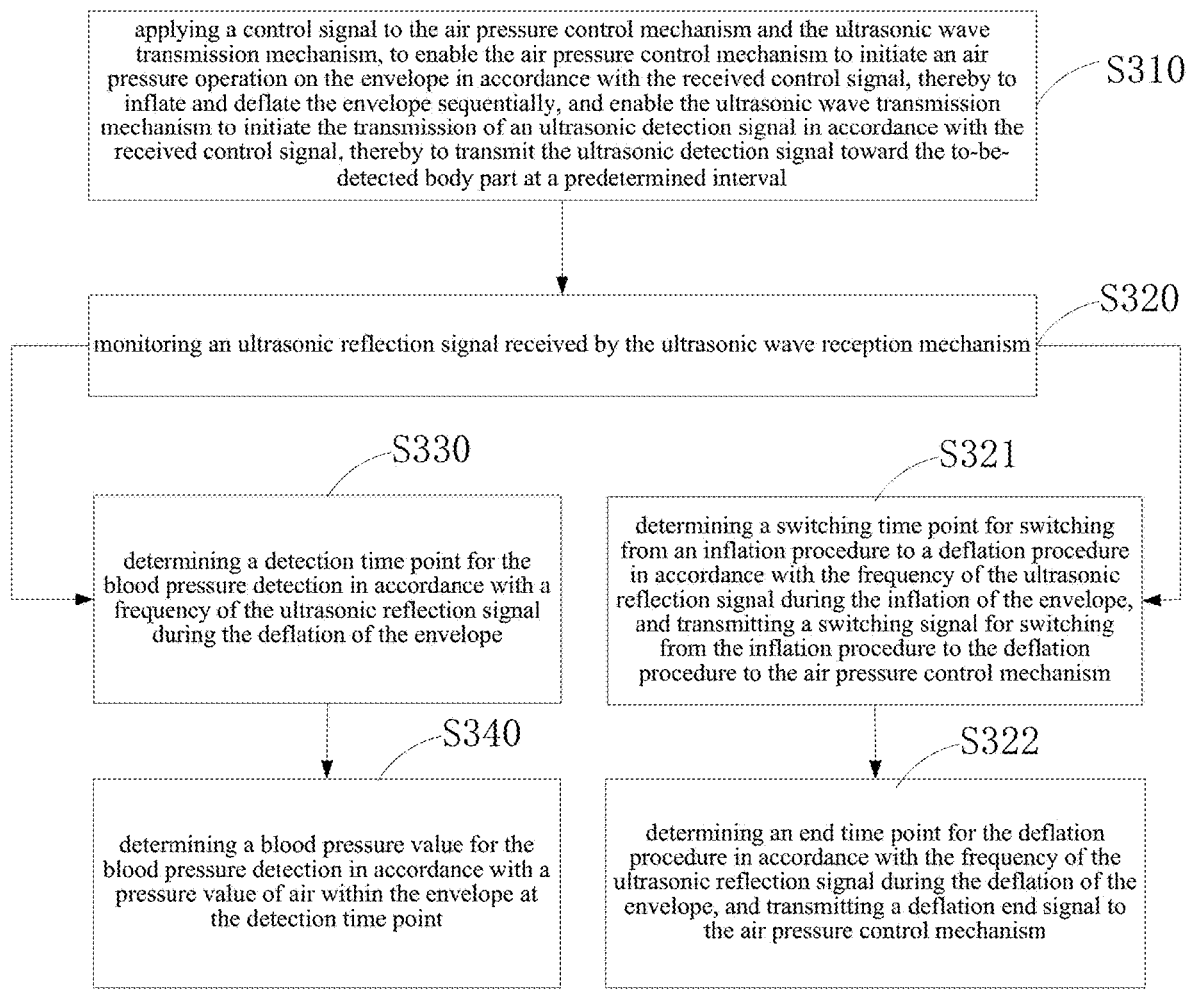
FIG. 3 is another flow chart of the blood pressure detection method according to some embodiments of the present disclosure.

In order to make the objects, the technical solutions and the advantages of the present disclosure more apparent, the present disclosure will be described hereinafter in a clear and complete manner in conjunction with the drawings and embodiments. Obviously, the following embodiments merely relate to a part of, rather than all of, the embodiments of the present disclosure, and based on these embodiments, a person skilled in the art may, without any creative effort, obtain the other embodiments, which also fall within the scope of the present disclosure.

Unless otherwise defined, any technical or scientific term used herein shall have the common meaning understood by a person of ordinary skills. Such words as "first" and "second" used in the specification and claims are merely used to differentiate different components rather than to represent any order, number or importance. Similarly, such words as "one" or "one of" are merely used to represent the existence of at least one member, rather than to limit the number thereof. Such words as "connect" or "connected to" may include electrical connection, direct or indirect, rather than to be limited to physical or mechanical connection. Such words as "on", "under", "left" and "right" are merely used to represent relative position relationship, and when an absolute position of the object is changed, the relative position relationship will be changed too.

The present disclosure provides in some embodiments a blood pressure detection method for a sphygmomanometer including an envelope for covering a to-be-detected body part during the blood pressure detection, an air pressure control mechanism configured to inflate and deflate the envelope, and an ultrasonic wave transmission mechanism and an ultrasonic wave reception mechanism arranged on the envelope. As shown in FIG. 1, in some embodiments, the blood pressure detection method includes: Step S110 of applying a control signal to the air pressure control mechanism and the ultrasonic wave transmission mechanism, to enable the air pressure control mechanism to initiate an air pressure operation on the envelope in accordance with the received control signal, thereby to inflate and deflate the envelope sequentially, and enable the ultrasonic wave transmission mechanism to initiate the transmission of an ultrasonic detection signal in accordance with the received control signal, thereby to transmit the ultrasonic detection signal toward the to-be-detected body part at a predetermined interval; Step S120 of monitoring an ultrasonic reflection signal received by the ultrasonic wave reception mechanism; Step S130 of determining a detection time point for the blood pressure detection in accordance with a frequency of the ultrasonic reflection signal during the deflation of the envelope; and Step S140 of determining a blood pressure value for the blood pressure detection in accordance with a pressure value of air within the envelope at the detection time point.

According to the blood pressure detection method in the embodiments of the present disclosure, on the basis of a principle of the ultrasonic detection mode where a frequency of an ultrasonic wave changes greatly at a critical point between a systolic pressure and a diastolic pressure due to a state of a vessel during the deflation of the sphygmomanometer, it is able to detect the change in the frequency of the ultrasonic wave during the deflation, so as to determine the critical point between the systolic pressure and the diastolic pressure, thereby to acquire the blood pressure value. In the embodiments of the present disclosure, a pressurized state of the vessel may be reflected by the frequency, in regardless of a flow speed of the blood. As a result, it is able to improve the detection accuracy even in the case that the flow speed of the blood changes due to the movement of the to-be-detected body part.

To be specific, in Step S130, the detection time point for the blood pressure detection may be determined in accordance with a change in the frequency of the ultrasonic reflection signal relative to the frequency of the ultrasonic detection signal during the deflation of the envelope.

In a possible embodiment of the present disclosure, in the above blood pressure detection method, during the inflation and deflation of the sphygmomanometer, the frequency of the ultrasonic detection signal transmitted by the ultrasonic wave transmission mechanism may be of a given value. In this way, it is merely able to determine the detection time point for the blood pressure detection by detecting the frequency of the ultrasonic reflection signal in Step S130.

The air pressure control mechanism of the sphygmomanometer may have a function identical to an inflatable sphygmomanometer in the related art, and it may include an air pump for performing the inflation and the deflation on the envelope sequentially during the blood pressure detection. The ultrasonic wave transmission mechanism on the envelope may be configured to, during the inflation and the deflation of the envelope, transmit the ultrasonic detection signal to the to-be-detected body part covered by the envelope at a predetermined interval. The ultrasonic wave reception mechanism on the envelope may be configured to receive the ultrasonic reflection signal generated after the ultrasonic detection signal has been reflected by the to-be-detected body part.

In the embodiments of the present disclosure, the blood pressure detection may be achieved on the basis of a principle that different influences on the difference between the frequencies of the ultrasonic transmission signal and the ultrasonic detection signal are caused by different movement states of a vascular wall of a vessel at the to-be-detected body part under the effect of an air pressure. To be specific, based on a sound wave transmission principle, there are the following relationships between the frequencies of the ultrasonic reflection signal and the ultrasonic detection signal and the movement states of the vascular wall:

$$f_D = f_T + \frac{2v}{c} f_T$$

$$\Delta f = f_D - f_T = \frac{2v}{C} f_T,$$

where $f_D$ represents the frequency of the ultrasonic reflection signal, $f_T$ represents the frequency of the ultrasonic detection signal, C represents a transmission speed of the sound wave in a medium, and v represents a relative movement speed of an movement object, i.e., the vascular wall, relative to the ultrasonic wave transmission mechanism.

Based on the above-mentioned equations, obviously the difference $f_D-f_T$ between the frequencies of the ultrasonic reflection signal and the ultrasonic detection signal is in direct proportion to the speed v of the vascular wall relative to the ultrasonic wave transmission mechanism.

Hence, based on the above relationships, during the inflation using the air pressure control mechanism, the vascular wall may be pressurized, so as to move from a fully-open state towards a close state. At the beginning of the inflation, the vascular wall is pressurized and moves toward the close state at a certain relative movement speed v, so there is a certain difference between the frequencies of the ultrasonic reflection signal and the ultrasonic detection signal, i.e., $f_D-f_T$. In the case that the vascular wall moves to the fully-close state, it continues to be pressurized until the vascular wall is incapable of moving any more. At this time, the relative movement speed v approaches to zero, and the difference $f_D-f_T$ approaches to zero too, so the inflation procedure may be ended.

During the deflation using the air pressure control mechanism, along with the decrease in the pressure, the vascular wall may move from the fully-close state towards the fully-open state. At the beginning of the deflation procedure, the vascular wall is in the fully-close state and the relative movement speed v approaches to zero. At this time, the difference between the frequencies of the ultrasonic reflections signal and the ultrasonic detection signal, i.e., $f_D-f_T$, approaches to zero. At the time point when the vascular wall moves from the fully-close state toward the open state, the vascular wall may have a certain relative movement speed v, so there is a certain difference $f_D-f_T$ between the frequencies. In the case that the vascular wall is in the fully-open state, it is incapable of moving anymore, and the relative movement speed v is zero. At this time, the difference $f_D-f_T$ between the frequencies approaches to zero.

To be specific, during the inflation and the deflation, the relationship between a state of the vascular wall and the difference between the sound wave frequencies may be shown in the following table:

| state of vascular wall | inflation | | deflation | |
|---|---|---|---|---|
| | time point when the vascular wall moves toward a fully-close state | time point when the vascular wall is in the fully-close state | time point when the vascular wall moves toward a fully-open state | time point when the vascular wall is in the fully-open state |
| $f_D$-$f_T$ | relatively small (30-100 hz) | approaching to zero | relatively large (200-500 hz) | approaching to zero |
| medical meaning | flow speed of the blood decreases | the blood creases to flow | systolic pressure (accelerated blood flow) | diastolic pressure (blood flow without hindrance) |

Based on the above-mentioned relationship, during the deflation, at the time point when the vascular wall moves from the fully-close state to the open state, the blood may flow in an accelerated manner, and this time point is just the detection time point for the systolic pressure. The difference $f_D$-$f_T$ between the sound wave frequencies may be varied from a value approaching to zero to a larger value, usually 200 to 500 Hz. Hence, it is able to detect the detection time point for the systolic pressure by monitoring the change in the difference $f_D$-$f_T$ during the deflation. At the time point when the vascular wall has been recovered to the fully-open state, the blood may flow without hindrance, and this time point is just the detection time point for the diastolic pressure. The difference $f_D$-$f_T$ between the sound wave frequencies may be varied from a larger value to a value approaching to zero. Hence, it is able to detect the detection time point for the diastolic pressure by monitoring the change in the difference $f_D$-$f_T$ during the deflation.

In the embodiments of the present disclosure, on the basis of the ultrasonic detection principle that there is relatively large ultrasonic frequency shift (i.e., the change in the frequency of the ultrasonic reflection signal relative to the frequency of the ultrasonic detection signal) at the critical point between the systolic pressure and the diastolic pressure during the deflation of the sphygmomanometer due to the state of the vessel, it is able to determine the critical point between the systolic pressure and the diastolic pressure by detecting the ultrasonic frequency shift during the deflation, thereby to acquire the blood pressure value.

Based on the above principle, as shown in FIG. 2, in Step S130, the step of determining the detection time point for the blood pressure detection in accordance with the frequency of the ultrasonic reflection signal during the deflation of the envelope may include: Step S131 of, during the deflation of the envelope, monitoring a difference between a frequency of the ultrasonic reflection signal and a frequency of the ultrasonic detection signal within each time period, i.e. detecting and obtaining a difference $f_D$-$f_T$; and Step S132 of comparing a difference between the frequency of the ultrasonic reflection signal and the frequency of the ultrasonic detection signal within a current time period with a difference between a frequency of the ultrasonic reflection signal and the frequency of the ultrasonic detection signal within each of the predetermined number of previous time periods previous to the current time period, so as to determine the detection time point for the blood pressure detection.

To be specific, Step S132 may include: in the case that an absolute value of the difference between the frequency of the ultrasonic reflection signal and the frequency of the ultrasonic detection signal within the current time period is greater than or equal to a first predetermined value, and an absolute value of the difference between the frequency of the ultrasonic reflection signal and the frequency of the ultrasonic detection signal within each of the predetermined number of previous time periods previous to the current time period is smaller than or equal to a second predetermined value, determining a reception time point for the ultrasonic reflection signal within the current time period as a detection time point for the detection of a systolic pressure; and in the case that the absolute value of the difference between the frequency of the ultrasonic reflection signal and the frequency of the ultrasonic detection signal within the current time period is smaller than or equal to the second predetermined value, and the absolute value of the difference between the frequency of the ultrasonic reflection signal and the frequency of the ultrasonic detection signal within each of the predetermined number of previous time periods previous to the current time period is greater than or equal to a third predetermined value, determining a reception time point for the ultrasonic reflection signal within the current time period as a detection time point for the detection of a diastolic pressure. The first predetermined value is greater than or equal to the third predetermined value, and the third predetermined value is greater than or equal to the second predetermined value.

To be specific, the second predetermined value may approach to zero. The first predetermined value may be smaller than the difference between the frequency of the ultrasonic reflection signal and the frequency of the ultrasonic detection signal at the time point when the vascular wall moves from the fully-close state to the open state, as long as the time point when the vascular wall moves from the fully-close state to the open state is capable of being monitored. It should be appreciated that, during the deflation, the movement speed of the vascular wall at the time point when the vascular wall moves from the fully-close state to the open state is greater than the movement speed of the vascular wall during the time period where the vascular wall moves from the open state to the fully-open state, so the third predetermined value for monitoring the time point when the vascular wall moves from the open state to the fully-open state may be smaller than the second predetermined value, as long as the time point when the vascular wall moves from the open state to the fully-open state is capable of being monitored.

It should be appreciated that, on the basis of the above-mentioned principle, the first predetermined value may also be equal to the third predetermined value, or the third predetermined value may be equal to the second predetermined value.

In the above Step S132, the predetermined number may refer to one or more, as long as the change in the frequency of the ultrasonic reflection signal relative to the frequency of the ultrasonic detection signal may be monitored.

In addition, in the above Step S131, the "time period" for monitoring may have a predetermined value from the beginning of the deflation to the end of the deflation. One predetermined time length may be one "time period". In Step S131 of monitoring the difference between the frequency of the ultrasonic reflection signal and the frequency of the ultrasonic detection signal within each time period may include monitoring a frequency of a first ultrasonic detection signal within each time period, and monitoring a frequency of a last ultrasonic reflection signal within each time period, so as to determine the difference between the frequency of the ultrasonic reflection signal and the frequency of the ultrasonic detection signal within each time period, i.e. detecting and obtaining a difference $f_D-f_T$. In a possible embodiment of the present disclosure, in order to ensure the detection accuracy, the value of each "time period" may be determined in accordance with a transmission frequency of the ultrasonic detection signal, so as to ensure that there is merely one ultrasonic detection signal and one ultrasonic reflection signal within each "time period". Alternatively, the value of the time period may also be determined in accordance with a minimum scale of a monitor.

In addition, in Step S132, in the case that each "time period" has a relatively small value, within a duration from the detection time point for the systolic pressure to the detection time point for the diastolic pressure, a change in the pressure may be omitted. Hence, any time point within the duration may be determined as the detection time point for the systolic pressure or the diastolic pressure.

In a possible embodiment of the present disclosure, in the case that the frequency of the ultrasonic detection signal transmitted by the ultrasonic wave transmission mechanism has a given value during the inflation and the deflation, the frequency of each of the received ultrasonic reflection signals may be compared with the frequency of each of the predetermined number of ultrasonic reflection signals received previously. In the case that the frequency of the currently-received ultrasonic reflection signal is greater than a first frequency and smaller than a second frequency, the reception time point for the currently-received ultrasonic reflection signal may be determined as the detection time point for the systolic pressure. In the case that the frequency of the currently-received ultrasonic reflection signal is smaller than the second frequency and greater than a third frequency, the reception time point for the ultrasonic reflection signal received in the current time period may be determined as the detection time point for the detection of the diastolic pressure. In Step 130, during the deflation of the envelope, in the case that the absolute value of the difference between the frequency of the ultrasonic reflection signal and the frequency of the ultrasonic detection signal is changed from a value smaller than or equal to the second predetermined value to a value greater than or equal to the first predetermined value, it may be determined that the detection time point for the detection of the systolic pressure has been monitored. In the case of detecting that the absolute value of the difference between the frequency of the ultrasonic reflection signal and the frequency of the ultrasonic detection signal is changed from a value greater than or equal to the third predetermined value to a value smaller than or equal to the second predetermined value, it may be determined that the detection time point for the detection of the diastolic pressure has been monitored.

Further, as shown in FIGS. 1 and 2, in Step S131, step of monitoring the difference between the frequency of the ultrasonic reflection signal and the frequency of the ultrasonic detection signal within each time period may include: acquiring a first frequency of the ultrasonic detection signal transmitted by the ultrasonic wave transmission mechanism at a start time point of each time period; acquiring a second frequency of the ultrasonic reflection signal received by the ultrasonic wave reception mechanism at an end time point of each time period; and calculating the difference in accordance with the second frequency and the first frequency.

According to the blood pressure detection method as shown in FIGS. 1 and 2, on the basis of the ultrasonic detection principle that a frequency shift is caused by the movement state of the vessel at the critical point between the systolic pressure and the diastolic pressure during the ultrasonic detection, it is able to determine the critical point between the systolic pressure and the diastolic pressure by detecting the change of the frequency shift, so as to acquire the detection pressure value. The blood pressure detection method in the embodiments of the present disclosure is different from the detection method in the related art, and it is regardless of the blood flow speed. As a result, it is able to improve the detection accuracy even in the case that the blood flow speed changes due to the movement of the to-be-detected body part.

In addition, according to the relationship between the state of the vascular wall and the change of the frequency shift of the ultrasonic wave during the inflation and deflation as shown in FIGS. 1 and 2, it is able for the blood pressure detection method in the embodiments of the present disclosure to determine, by detecting the change of the frequency shift, the end time points for the inflation and deflation procedures, apart from determining the detection time points for the systolic pressure and the diastolic pressure.

In some embodiments of the present disclosure, as shown in FIG. 3, similar as shown in FIGS. 1 and 2, another blood pressure detection method may include: Step S310 of applying a control signal to the air pressure control mechanism and the ultrasonic wave transmission mechanism, to enable the air pressure control mechanism to initiate an air pressure operation on the envelope in accordance with the received control signal, thereby to inflate and deflate the envelope sequentially, and enable the ultrasonic wave transmission mechanism to initiate the transmission of an ultrasonic detection signal in accordance with the received control signal, thereby to transmit the ultrasonic detection signal toward the to-be-detected body part at a predetermined interval; Step S320 of monitoring an ultrasonic reflection signal received by the ultrasonic wave reception mechanism; Step S330 of determining a detection time point for the blood pressure detection in accordance with a frequency of the ultrasonic reflection signal during the deflation of the envelope; and Step S340 of determining a blood pressure value for the blood pressure detection in accordance with a pressure value of air within the envelope at the detection time point.

In Step S330, the mode of determining the detection time point for the blood pressure detection in accordance with the frequency of the ultrasonic reflection signal during the deflation of the envelope is identical to that mentioned in Step S130 in the embodiment of FIGS. 1 and 2, and thus will not be particularly defined herein.

In addition, in this embodiment, as shown in FIG. 3, subsequent to Step S320, the blood detection method may further include: Step S321 of determining a switching time point for switching from an inflation procedure to a deflation procedure in accordance with the frequency of the ultrasonic reflection signal during the inflation of the envelope, and transmitting a switching signal for switching from the inflation procedure to the deflation procedure to the air pressure control mechanism; and Step S322 of determining an end time point for the deflation procedure in accordance with the frequency of the ultrasonic reflection signal during the deflation of the envelope, and transmitting a deflation end signal to the air pressure control mechanism.

To be specific, Step S321 may include: during the inflation of the envelope, monitoring a difference between the frequency of the ultrasonic reflection signal and the frequency of the ultrasonic detection signal within each time period; and in the case that an absolute value of a difference between the frequency of the ultrasonic reflection signal and the frequency of the ultrasonic detection signal within a current time period is smaller than or equal to a fourth predetermined value, and an absolute value of a difference between the frequency of the ultrasonic reflection signal and the frequency of the ultrasonic detection signal within each of the predetermined number of previous time periods previous to the current time period is greater than the fourth predetermined value, determining a reception time point for the ultrasonic reflection signal within the current time period as the switching time point for switching from the inflation procedure to the deflation procedure.

To be specific, Step S322 may include: during the deflation of the envelope, monitoring a difference between a frequency of the ultrasonic reflection signal and the frequency of the ultrasonic detection signal within each time period; and in the case that an absolute value of a difference between the frequency of the ultrasonic reflection signal and the frequency of the ultrasonic detection signal within the current time period is smaller than or equal to the fourth predetermined value, and an absolute value of a difference between the frequency of the ultrasonic reflection signal and the frequency of the ultrasonic detection signal within each of the predetermined number of previous time periods previous to the current time period is greater than the fourth predetermined value, determining a reception time point for the ultrasonic reflection signal within the current time period as the end time point for the deflation procedure.

In the above steps, the determination of the "time period", the switching time point from the inflation procedure to the deflation procedure, and the end time point of the inflation procedure may refer to the determination of the "time period", the detection time point for the systolic pressure and the detection time point for the diastolic pressure mentioned hereinabove in the embodiment of FIGS. 1 and 2, and thus will not be particularly defined herein.

On the basis of the relationship between the movement state of the vascular wall and the difference between the sound wave frequencies during the inflation and the deflation as shown in FIG. 3, the during the inflation using the air pressure control mechanism, in the case that the vascular wall is pressurized and moves from the fully-open state to the fully-close state, the relative movement speed of the vascular wall may approach to zero from a certain speed, so the difference between the sound wave frequencies, i.e., $f_D-f_T$, may approach to zero too from a certain value. Hence, during the inflation, in the case of detecting that the difference between the sound wave frequencies, i.e., $f_D-f_T$, within a current time period is changed from a value greater than the fourth predetermined value to a value smaller than or equal to the fourth predetermined value, the reception time point for the ultrasonic reflection signal within the current time period may be determined as the switching time point for switching from the inflation procedure to the deflation procedure. The fourth predetermined value is a value approaching to zero. During the deflation using the air pressure control mechanism, the vascular wall moves from the fully-close state to the fully-open state, the relative movement speed of the vascular wall approaches to zero from a certain speed, so the difference between the sound wave frequencies, i.e., $f_D-f_T$, may approach to zero too from a certain value. As a result, during the deflation, in the case of detecting that the difference between the sound wave frequencies within the current time period, i.e., $f_D-f_T$, is changed from a value greater than the fourth predetermined value to a value smaller than or equal to the fourth predetermined value, the reception time point for the ultrasonic reflection signal within the current time period may be determined as the end time point for the deflation procedure.

As mentioned above, by detecting the change of the ultrasonic frequency shift, it is able for the blood pressure detection method in the embodiments of the present disclosure to determine the detection time points for the systolic pressure and the diastolic pressure, and determine the end time points for the inflation and deflation procedures.

In Steps S321 and S322, the step of monitoring the difference between the frequency of the ultrasonic reflection signal and the frequency of the ultrasonic detection signal within each time period may include: acquiring a first frequency of the ultrasonic detection signal transmitted by the ultrasonic wave transmission mechanism at a start time point of each time period; acquiring a second frequency of the ultrasonic reflection signal received by the ultrasonic wave reception mechanism at an end time point of each time period; and calculating the difference in accordance with the second frequency and the first frequency.

In addition, in the embodiment of FIGS. 1, 2 and the embodiment of FIG. 3, the step of determining the blood pressure value for the blood pressure detection in accordance with the pressure value of the air within the envelope at the detection time point may include: detecting a pressure value outputted by the air pressure control mechanism at the detection time point; and setting the pressure value outputted by the air pressure control mechanism at the detection time point as the pressure value of the air within the envelope, and setting the pressure value of the air within the envelope as the blood pressure value.

Through the above-mentioned steps, in the case that the detection time point has been monitored, it is able to acquire the blood pressure value by determining the pressure value outputted by the air pressure control mechanism at a time point corresponding to the detection time point.

Figure 4:
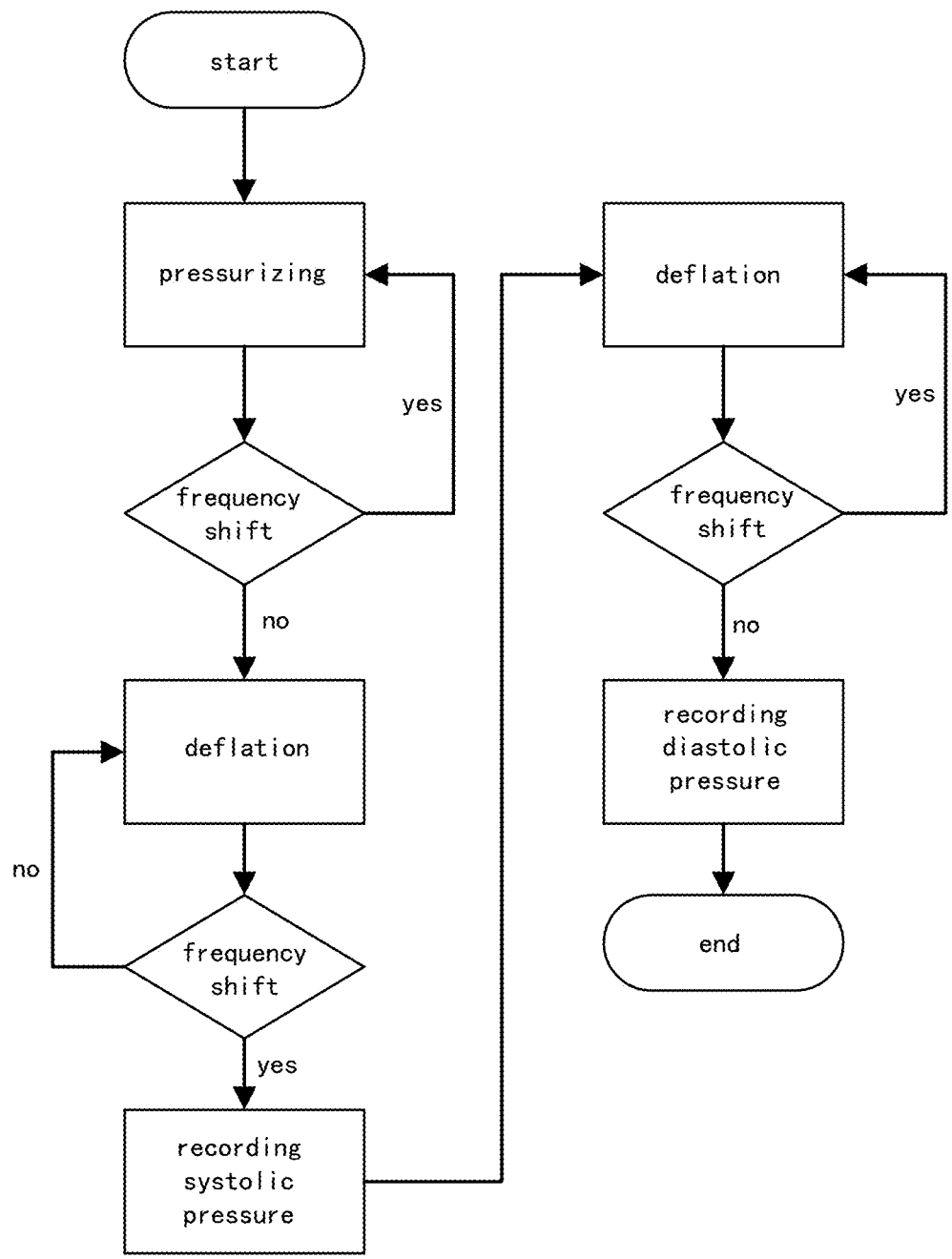
FIG. 4 is yet another flow chart of the blood pressure detection method according to the embodiment of FIG. 3 of the present disclosure.

According to the blood pressure detection method as shown in FIG. 3, during the inflation and deflation, in the case that the vascular wall is pressurized and moves from the open state to the fully-close state and from the close state to the fully-open state, the time point when the absolute value of the difference between the frequency of the ultrasonic reflection signal and the frequency of the ultrasonic detection signal within the current time period (i.e., the change of the ultrasonic frequency shift) is changed to zero from a certain value may be set as a monitoring condition. At this time, as shown in FIG. 4, the blood pressure detection method may include the steps of: starting the inflation procedure; continuing the inflation procedure in the case of detecting that the frequency shift within the current time period is not zero; starting the deflation procedure in the case that the frequency shift within the current time period is zero; during the deflation, in the case of detecting that the frequency shift within the current time period is zero, continuing the deflation procedure; in the case of detecting that the frequency shift within the current time period is switched from zero to a certain value, recoding a current pressure value outputted by the air pressure control mechanism as the systolic pressure, and continuing the deflation procedure; in the case of detecting that the frequency shift within the current time period is not zero, continuing the deflation procedure; and in the case of detecting that the frequency shift within the current time period is switched from a certain value to zero, recording a current pressure value outputted by the air pressure control mechanism currently as the diastolic pressure, and terminating the deflation procedure.

Figure 5:
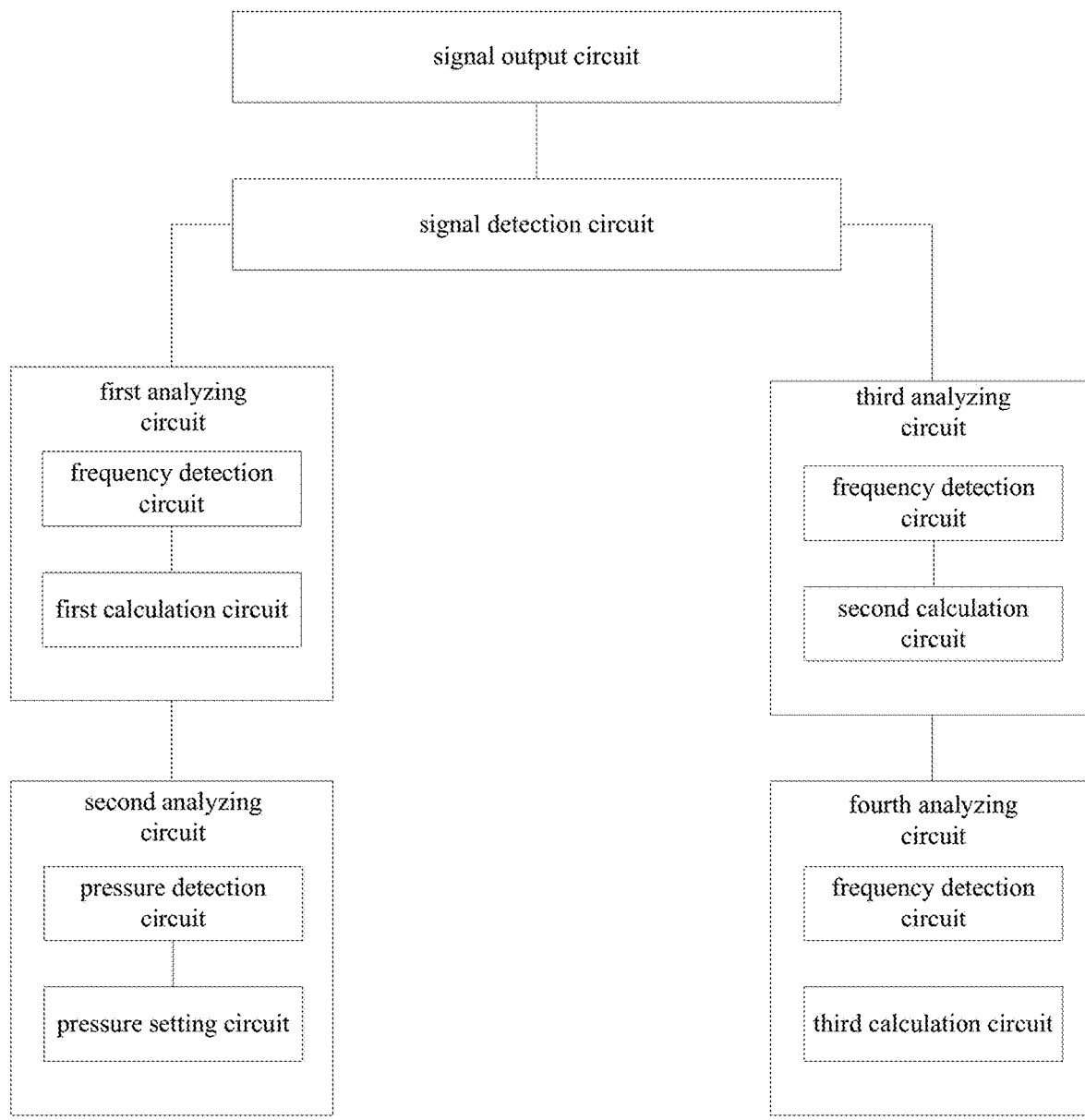
FIG. 5 is a partial schematic view showing a sphygmomanometer according to some embodiments of the present disclosure.

The present disclosure further provides in some embodiments a sphygmomanometer including an envelope for covering a to-be-detected body part during the blood pressure detection, an air pressure control mechanism configured to inflate and deflate the envelope, and an ultrasonic wave transmission mechanism and an ultrasonic wave reception mechanism arranged on the envelope. As shown in FIG. 5, the sphygmomanometer may further include: a signal output circuit configured to apply a control signal to the air pressure control mechanism and the ultrasonic wave transmission mechanism, to enable the air pressure control mechanism to initiate an air pressure operation on the envelope in accordance with the received control signal, thereby to inflate and deflate the envelope sequentially, and enable the ultrasonic wave transmission mechanism to initiate the transmission of an ultrasonic detection signal in accordance with the received control signal, thereby to transmit the ultrasonic detection signal toward the to-be-detected body part at a predetermined interval; a signal detection circuit configured to monitor an ultrasonic reflection signal received by the ultrasonic wave reception mechanism; a first analyzing circuit configured to determine a detection time point for the blood pressure detection in accordance with a frequency of the ultrasonic reflection signal during the deflation of the envelope; and a second analyzing circuit configured to determine a blood pressure value for the blood pressure detection in accordance with a pressure value of air within the envelope at the detection time point.

According to the sphygmomanometer in the embodiments of the present disclosure, it is able to determine the critical point between the systolic pressure and the diastolic pressure by detecting the change of the frequency shift (i.e., the change in the frequency of the ultrasonic reflection signal relative to the frequency of the ultrasonic detection signal) during the deflation procedure, thereby to acquire the blood pressure value. In the embodiments of the present disclosure, a pressurized state of the vessel may be reflected by the frequency shift, in regardless of a flow speed of the blood. As a result, it is able to improve the detection accuracy even in the case that the flow speed of the blood changes due to the movement of the to-be-detected body part.

As shown in FIG. 5, the first analyzing circuit may include: a frequency detection circuit configured to, during the deflation of the envelope, monitor a difference between a frequency of the ultrasonic reflection signal and a frequency of the ultrasonic detection signal within each time period; and a first calculation circuit configured to compare a difference between the frequency of the ultrasonic reflection signal and the frequency of the ultrasonic detection signal within a current time period with a difference between a frequency of the ultrasonic reflection signal and the frequency of the ultrasonic detection signal within each of the predetermined number of previous time periods previous to the current time period, so as to determine the detection time point for the blood pressure detection.

To be specific, the first calculation circuit may be further configured to: in the case that an absolute value of the difference between the frequency of the ultrasonic reflection signal and the frequency of the ultrasonic detection signal within the current time period is greater than or equal to a first predetermined value, and an absolute value of the difference between the frequency of the ultrasonic reflection signal and the frequency of the ultrasonic detection signal within each of the predetermined number of previous time periods previous to the current time period is smaller than or equal to a second predetermined value, determine a reception time point for the ultrasonic reflection signal within the current time period as a detection time point for the detection of a systolic pressure; and in the case that the absolute value of the difference between the frequency of the ultrasonic reflection signal and the frequency of the ultrasonic detection signal within the current time period is smaller than or equal to the second predetermined value, and the absolute value of the difference between the frequency of the ultrasonic reflection signal and the frequency of the ultrasonic detection signal within each of the predetermined number of previous time periods previous to the current time period is greater than or equal to a third predetermined value, determine a reception time point for the ultrasonic reflection signal within the current time period as a detection time point for the detection of a diastolic pressure. The first predetermined value is greater than or equal to the third predetermined value, and the third predetermined value is greater than or equal to the second predetermined value.

In a possible embodiment of the present disclosure, as shown in FIG. 5, the sphygmomanometer may further include: a third analyzing circuit configured to determine a switching time point for switching from an inflation procedure to a deflation procedure in accordance with the frequency of the ultrasonic reflection signal during the inflation of the envelope, and transmit a switching signal for switching from the inflation procedure to the deflation procedure to the air pressure control mechanism; and a fourth analyzing circuit configured to determine an end time point for the deflation procedure in accordance with the frequency of the ultrasonic reflection signal during the deflation of the envelope, and transmit a deflation end signal to the air pressure control mechanism.

In the embodiments of the present disclosure, the third analyzing circuit may determine the switching time point for switching from the inflation procedure to the deflation procedure in accordance with the change in the frequency of the ultrasonic reflection signal relative to the frequency of the ultrasonic detection signal during the inflation of the envelope. The fourth analyzing circuit may determine the end time point for the deflation procedure in accordance with the change in the frequency of the ultrasonic reflection signal relative to the frequency of the ultrasonic detection signal during the deflation of the envelope.

To be specific, the third analyzing circuit may include: a frequency detection circuit configured to, during the inflation of the envelope, monitor a difference between the frequency of the ultrasonic reflection signal and the frequency of the ultrasonic detection signal within each time period; and a second calculation circuit configured to, in the case that an absolute value of a difference between the frequency of the ultrasonic reflection signal and the frequency of the ultrasonic detection signal within a current time period is smaller than or equal to a fourth predetermined value, and an absolute value of a difference between the frequency of the ultrasonic reflection signal and the frequency of the ultrasonic detection signal within each of the predetermined number of previous time periods previous to the current time period is greater than the fourth predetermined value, determine a reception time point for the ultrasonic reflection signal within the current time period as the switching time point for switching from the inflation procedure to the deflation procedure.

To be specific, the fourth analyzing circuit may include: a frequency detection circuit configured to, during the deflation of the envelope, monitor a difference between a frequency of the ultrasonic reflection signal and the frequency of the ultrasonic detection signal within each time period; and a third calculation circuit configured to, in the case that an absolute value of a difference between the frequency of the ultrasonic reflection signal and the frequency of the ultrasonic detection signal within the current time period is smaller than or equal to the fourth predetermined value, and an absolute value of a difference between the frequency of the ultrasonic reflection signal and the frequency of the ultrasonic detection signal within each of the predetermined number of previous time periods previous to the current time period is greater than the fourth predetermined value, determine a reception time point for the ultrasonic reflection signal within the current time period as the end time point for the deflation procedure.

According to the sphygmomanometer in the embodiments of the present disclosure, through detecting the frequency shift, it is able to determine the detection time points for the systolic pressure and the diastolic pressure, as well as the end time points for the inflation procedure and the deflation procedure.

To be specific, the frequency detection circuit may include: a first frequency acquisition circuit configured to acquire a first frequency of the ultrasonic detection signal transmitted by the ultrasonic wave transmission mechanism at a start time point of each time period; a second frequency acquisition circuit configured to acquire a second frequency of the ultrasonic reflection signal received by the ultrasonic wave reception mechanism at an end time point of each time period; and a difference calculation circuit configured to calculate the difference in accordance with the second frequency and the first frequency.

In addition, as shown in FIG. 5, the second analyzing circuit may include: a pressure detection circuit configured to detect a pressure value outputted by the air pressure control mechanism at the detection time point; and a pressure setting circuit configured to set the pressure value outputted by the air pressure control mechanism at the detection time point as the pressure value of the air within the envelope, and set the pressure value of the air within the envelope as the blood pressure value.

In the embodiments of the present disclosure, the sphygmomanometer may include the envelope for covering the to-be-detected body part, the air pressure control mechanism configured to perform the inflation and deflation procedures, the ultrasonic wave transmission mechanism and the ultrasonic wave reception mechanism arranged on the envelope, and chips of the above-mentioned circuits.

To be specific, the ultrasonic wave transmission mechanism and the ultrasonic wave reception mechanism may be arranged on the envelope. The ultrasonic wave transmission mechanism may be configured to transmit the ultrasonic detection signal toward the to-be-detected body part covered by the envelope, and the ultrasonic wave reception mechanism may be configured to acquire the ultrasonic reflection signal generated after the ultrasonic detection signal has been reflected by the to-be-detected body part. In a possible embodiment of the present disclosure, the signal output circuit, the signal detection circuit, the first analyzing circuit and the second analyzing circuit in the sphygmomanometer may be integrated into one chip and then arranged on the envelope, so as to apply the control signal to the ultrasonic wave transmission mechanism and acquire the signal fed back by the ultrasonic wave reception mechanism.

Furthermore, the air pressure control mechanism may also be arranged on the envelope, or connected to the envelope through a connection line, as long as the signal transmission may be achieved between the air pressure control mechanism and a blood detection device.

In a possible embodiment of the present disclosure, the envelope may be of a size matching a size of a finger or toe of a human body, so that the envelope may cover the finger or toe for the subsequent blood pressure detection. As compared with the related art where the blood pressure detection is performed with respect to the arm, in the embodiments of the present disclosure, it is able for the sphygmomanometer to detect the blood pressure at a peripheral body part without interfering with user's rest and exercise, thereby to further improve the detection accuracy even in the case of movement.

In a possible embodiment of the present disclosure, the sphygmomanometer may further include a wireless transmission circuit, e.g., a Bluetooth circuit, for transmitting the acquired blood pressure value to a terminal device.

According to the sphygmomanometer in the embodiments of the present disclosure, the blood pressure may be detected through ultrasonic waves. In addition, during the detection, the pressurized state of the vessel may be reflected by the frequency shift, regardless of the blood flow speed. As a result, it is able to improve the detection accuracy even in the case that the blood flow speed changes due to the movement of the to-be-detected body part.

The above are merely the preferred embodiments of the present disclosure, but the present disclosure is not limited thereto. Obviously, a person skilled in the art may make further modifications and improvements without departing from the spirit of the present disclosure, and these modifications and improvements shall also fall within the scope of the present disclosure.

What is claimed is:

1. A blood pressure detection method for a sphygmomanometer, wherein the sphygmomanometer comprises an envelope configured to cover a to-be-detected body part during the blood pressure detection, an air pressure control mechanism configured to inflate and deflate the envelope, and an ultrasonic wave transmission mechanism and an ultrasonic wave reception mechanism arranged on the envelope, the blood pressure detection method comprising:

applying a first control signal to the air pressure control mechanism and applying a second control signal to the ultrasonic wave transmission mechanism, to enable the air pressure control mechanism to initiate an air pressure operation on the envelope in accordance with the received first control signal, thereby to inflate and deflate the envelope sequentially, and enable the ultrasonic wave transmission mechanism to initiate transmission of an ultrasonic signal in accordance with the received second control signal, thereby to emit the ultrasonic signal toward the to-be-detected body part at a predetermined interval;

monitoring an ultrasonic reflection signal received by the ultrasonic wave reception mechanism;

determining a detection time point for the blood pressure detection in accordance with a frequency of the ultrasonic reflection signal during the deflation of the envelope; and determining a blood pressure value for the blood pressure detection in accordance with a pressure value of air within the envelope at the detection time point.

2. The blood pressure detection method according to claim 1, wherein the step of determining the detection time point for the blood pressure detection in accordance with the frequency of the ultrasonic reflection signal during the deflation of the envelope comprises:

during the deflation of the envelope, monitoring a difference between a frequency of the ultrasonic reflection signal and a frequency of the emitted ultrasonic signal within each time period; and comparing a difference between the frequency of the ultrasonic reflection signal and the frequency of the emitted ultrasonic signal within a current time period with a difference between a frequency of the ultrasonic reflection signal and the frequency of the emitted ultrasonic signal within each of the predetermined number of previous time periods previous to the current time period, to determine the detection time point for the blood pressure detection.

3. The blood pressure detection method according to claim 2, wherein the step of comparing the difference between the frequency of the ultrasonic reflection signal and the frequency of the emitted ultrasonic signal within the current time period with the difference between the frequency of the ultrasonic reflection signal and the frequency of the emitted ultrasonic signal within each of the predetermined number of previous time periods previous to the current time period, to determine the detection time point for the blood pressure detection comprises:

in the case that an absolute value of the difference between the frequency of the ultrasonic reflection signal and the frequency of the emitted ultrasonic signal within the current time period is greater than or equal to a first predetermined value, and an absolute value of the difference between the frequency of the ultrasonic reflection signal and the frequency of the emitted ultrasonic signal within each of the predetermined number of previous time periods previous to the current time period is smaller than or equal to a second predetermined value, determining a reception time point for the ultrasonic reflection signal within the current time period as a time point for the detection of a systolic pressure; and in the case that the absolute value of the difference between the frequency of the ultrasonic reflection signal and the frequency of the emitted ultrasonic signal within the current time period is smaller than or equal to the second predetermined value, and the absolute value of the difference between the frequency of the ultrasonic reflection signal and the frequency of the emitted ultrasonic signal within each of the predetermined number of previous time periods previous to the current time period is greater than or equal to a third predetermined value, determining a reception time point for the ultrasonic reflection signal within the current time period as a detection time point for the detection of a diastolic pressure, wherein the first predetermined value is greater than or equal to the third predetermined value, and the third predetermined value is greater than or equal to the second predetermined value.

4. The blood pressure detection method according to claim 1, wherein the step of determining the blood pressure value for the blood pressure detection in accordance with the pressure value of the air within the envelope at the detection time point comprises:

detecting a pressure value outputted by the air pressure control mechanism at the detection time point; and setting the pressure value outputted by the air pressure control mechanism at the detection time point as the pressure value of the air within the envelope, and setting the pressure value of the air within the envelope as the blood pressure value.

5. The blood pressure detection method according to claim 1, wherein subsequent to the step of monitoring the ultrasonic reflection signal received by the ultrasonic wave reception mechanism, the blood pressure detection method further comprises:

determining a switching time point for switching from an inflation procedure to a deflation procedure in accordance with the frequency of the ultrasonic reflection signal during the inflation of the envelope, and transmitting a switching signal for switching from the inflation procedure to the deflation procedure to the air pressure control mechanism; and determining an end time point for the deflation procedure in accordance with the frequency of the ultrasonic reflection signal during the deflation of the envelope, and transmitting a deflation end signal to the air pressure control mechanism.

6. The blood pressure detection method according to claim 5, wherein the step of determining the switching time point for switching from the inflation procedure to the deflation procedure in accordance with the frequency of the ultrasonic reflection signal during the inflation of the envelope comprises:

during the inflation of the envelope, monitoring a difference between the frequency of the ultrasonic reflection signal and the frequency of the emitted ultrasonic signal within each time period; and in the case that an absolute value of a difference between the frequency of the ultrasonic reflection signal and the frequency of the emitted ultrasonic signal within a current time period is smaller than or equal to a fourth predetermined value, and an absolute value of a difference between the frequency of the ultrasonic reflection signal and the frequency of the emitted ultrasonic signal within each of the predetermined number of previous time periods previous to the current time period is greater than the fourth predetermined value, determining a reception time point for the ultrasonic reflection signal within the current time period as the switching time point for switching from the inflation procedure to the deflation procedure, and the step of determining the end time point for the deflation procedure in accordance with the frequency of the ultrasonic reflection signal during the deflation of the envelope comprises:

during the deflation of the envelope, monitoring a difference between a frequency of the ultrasonic reflection signal and the frequency of the emitted ultrasonic signal within each time period; and in the case that an absolute value of a difference between the frequency of the ultrasonic reflection signal and the frequency of the emitted ultrasonic signal within the current time period is smaller than or equal to the fourth predetermined value, and an absolute value of a difference between the frequency of the ultrasonic reflection signal and the frequency of the emitted ultrasonic signal within each of the predetermined number of previous time periods previous to the current time period is greater than the fourth predetermined value, determining a reception time point for the ultrasonic reflection signal within the current time period as the end time point for the deflation procedure.

7. The blood pressure detection method according to claim 2, wherein the step of monitoring the difference between the frequency of the ultrasonic reflection signal and the frequency of the emitted ultrasonic signal within each time period comprises:
 acquiring a first frequency of the ultrasonic signal emitted by the ultrasonic wave transmission mechanism at a start time point of each time period;
 acquiring a second frequency of the ultrasonic reflection signal received by the ultrasonic wave reception mechanism at an end time point of each time period; and
 calculating the difference in accordance with the second frequency and the first frequency.

8. The blood pressure detection method according to claim 5, wherein the step of monitoring the difference between the frequency of the ultrasonic reflection signal and the frequency of the emitted ultrasonic signal within each time period comprises:
 acquiring a first frequency of the ultrasonic signal emitted by the ultrasonic wave transmission mechanism at a start time point of each time period;
 acquiring a second frequency of the ultrasonic reflection signal received by the ultrasonic wave reception mechanism at an end time point of each time period; and
 calculating the difference in accordance with the second frequency and the first frequency.

9. The blood pressure detection method according to claim 2, wherein subsequent to the step of monitoring the ultrasonic reflection signal received by the ultrasonic wave reception mechanism, the blood pressure detection method further comprises:
 determining a switching time point for switching from an inflation procedure to a deflation procedure in accordance with the frequency of the ultrasonic reflection signal during the inflation of the envelope, and transmitting a switching signal for switching from the inflation procedure to the deflation procedure to the air pressure control mechanism; and
 determining an end time point for the deflation procedure in accordance with the frequency of the ultrasonic reflection signal during the deflation of the envelope, and transmitting a deflation end signal to the air pressure control mechanism.

10. The blood pressure detection method according to claim 9, wherein the step of determining the switching time point for switching from the inflation procedure to the deflation procedure in accordance with the frequency of the ultrasonic reflection signal during the inflation of the envelope comprises:
 during the inflation of the envelope, monitoring a difference between the frequency of the ultrasonic reflection signal and the frequency of the emitted ultrasonic signal within each time period; and
 in the case that an absolute value of a difference between the frequency of the ultrasonic reflection signal and the frequency of the emitted ultrasonic signal within a current time period is smaller than or equal to a fourth predetermined value, and an absolute value of a difference between the frequency of the ultrasonic reflection signal and the frequency of the emitted ultrasonic signal within each of the predetermined number of previous time periods previous to the current time period is greater than the fourth predetermined value, determining a reception time point for the ultrasonic reflection signal within the current time period as the switching time point for switching from the inflation procedure to the deflation procedure, and
the step of determining the end time point for the deflation procedure in accordance with the frequency of the ultrasonic reflection signal during the deflation of the envelope comprises:
 during the deflation of the envelope, monitoring a difference between a frequency of the ultrasonic reflection signal and the frequency of the emitted ultrasonic signal within each time period; and
 in the case that an absolute value of a difference between the frequency of the ultrasonic reflection signal and the frequency of the emitted ultrasonic signal within the current time period is smaller than or equal to the fourth predetermined value, and an absolute value of a difference between the frequency of the ultrasonic reflection signal and the frequency of the emitted ultrasonic signal within each of the predetermined number of previous time periods previous to the current time period is greater than the fourth predetermined value, determining a reception time point for the ultrasonic reflection signal within the current time period as the end time point for the deflation procedure.

11. The blood pressure detection method according to claim 10, wherein the step of monitoring the difference between the frequency of the ultrasonic reflection signal and the frequency of the emitted ultrasonic signal within each time period comprises:
 acquiring a first frequency of the ultrasonic signal emitted by the ultrasonic wave transmission mechanism at a start time point of each time period;
 acquiring a second frequency of the ultrasonic reflection signal received by the ultrasonic wave reception mechanism at an end time point of each time period; and
 calculating the difference in accordance with the second frequency and the first frequency.

12. A sphygmomanometer comprising: an envelope configured to cover a to-be-detected body part during the blood pressure detection, an air pressure control mechanism configured to inflate and deflate the envelope, and an ultrasonic wave transmission mechanism and an ultrasonic wave reception mechanism arranged on the envelope, wherein the sphygmomanometer further comprises:
 a signal output circuit configured to apply a first control signal to the air pressure control mechanism and apply a second control signal to the ultrasonic wave transmission mechanism, to enable the air pressure control mechanism to initiate an air pressure operation on the envelope in accordance with the received first control signal, thereby to inflate and deflate the envelope sequentially, and enable the ultrasonic wave transmission mechanism to initiate transmission of an ultrasonic signal in accordance with the received second control signal, thereby to emit the ultrasonic signal toward the to-be-detected body part at a predetermined interval;

a signal detection circuit configured to monitor an ultrasonic reflection signal received by the ultrasonic wave reception mechanism;
a first analyzing circuit configured to determine a detection time point for the blood pressure detection in accordance with a frequency of the ultrasonic reflection signal during the deflation of the envelope; and
a second analyzing circuit configured to determine a blood pressure value for the blood pressure detection in accordance with a pressure value of air within the envelope at the detection time point.

13. The sphygmomanometer according to claim 12, wherein the first analyzing circuit comprises:
a frequency detection circuit configured to, during the deflation of the envelope, monitor a difference between a frequency of the ultrasonic reflection signal and a frequency of the emitted ultrasonic signal within each time period; and
a first calculation circuit configured to compare a difference between the frequency of the ultrasonic reflection signal and the frequency of the emitted ultrasonic signal within a current time period with a difference between a frequency of the ultrasonic reflection signal and the frequency of the emitted ultrasonic signal within each of the predetermined number of previous time periods previous to the current time period, to determine the detection time point for the blood pressure detection.

14. The sphygmomanometer according to claim 13, wherein the first calculation circuit is further configured to:
in the case that an absolute value of the difference between the frequency of the ultrasonic reflection signal and the frequency of the emitted ultrasonic signal within the current time period is greater than or equal to a first predetermined value, and an absolute value of the difference between the frequency of the ultrasonic reflection signal and the frequency of the emitted ultrasonic signal within each of the predetermined number of previous time periods previous to the current time period is smaller than or equal to a second predetermined value, determine a reception time point for the ultrasonic reflection signal within the current time period as a detection time point for the detection of a systolic pressure; and
in the case that the absolute value of the difference between the frequency of the ultrasonic reflection signal and the frequency of the emitted ultrasonic signal within the current time period is smaller than or equal to the second predetermined value, and the absolute value of the difference between the frequency of the ultrasonic reflection signal and the frequency of the emitted ultrasonic signal within each of the predetermined number of previous time periods previous to the current time period is greater than or equal to a third predetermined value, determine a reception time point for the ultrasonic reflection signal within the current time period as a detection time point for the detection of a diastolic pressure,
wherein the first predetermined value is greater than or equal to the third predetermined value, and the third predetermined value is greater than or equal to the second predetermined value.

15. The sphygmomanometer according to claim 12, wherein the second analyzing circuit comprises:
a pressure detection circuit configured to detect a pressure value outputted by the air pressure control mechanism at the detection time point; and a pressure setting circuit configured to set the pressure value outputted by the air pressure control mechanism at the detection time point as the pressure value of the air within the envelope, and set the pressure value of the air within the envelope as the blood pressure value.

16. The sphygmomanometer according to claim 12, further comprising:
a third analyzing circuit configured to determine a switching time point for switching from an inflation procedure to a deflation procedure in accordance with the frequency of the ultrasonic reflection signal during the inflation of the envelope, and transmit a switching signal for switching from the inflation procedure to the deflation procedure to the air pressure control mechanism; and
a fourth analyzing circuit configured to determine an end time point for the deflation procedure in accordance with the frequency of the ultrasonic reflection signal during the deflation of the envelope, and transmit a deflation end signal to the air pressure control mechanism.

17. The sphygmomanometer according to claim 16, wherein the third analyzing circuit comprises:
a frequency detection circuit configured to, during the inflation of the envelope, monitor a difference between the frequency of the ultrasonic reflection signal and the frequency of the emitted ultrasonic signal within each time period; and
a second calculation circuit configured to, in the case that an absolute value of a difference between the frequency of the ultrasonic reflection signal and the frequency of the emitted ultrasonic signal within a current time period is smaller than or equal to a fourth predetermined value, and an absolute value of a difference between the frequency of the ultrasonic reflection signal and the frequency of the emitted ultrasonic signal within each of the predetermined number of previous time periods previous to the current time period is greater than the fourth predetermined value, determine a reception time point for the ultrasonic reflection signal within the current time period as the switching time point for switching from the inflation procedure to the deflation procedure,
wherein the fourth analyzing circuit comprises:
a frequency detection circuit configured to, during the deflation of the envelope, monitor a difference between a frequency of the ultrasonic reflection signal and the frequency of the emitted ultrasonic signal within each time period; and
a third calculation circuit configured to, in the case that an absolute value of a difference between the frequency of the ultrasonic reflection signal and the frequency of the emitted ultrasonic signal within the current time period is smaller than or equal to the fourth predetermined value, and an absolute value of a difference between the frequency of the ultrasonic reflection signal and the frequency of the emitted ultrasonic signal within each of the predetermined number of previous time periods previous to the current time period is greater than the fourth predetermined value, determine a reception time point for the ultrasonic reflection signal within the current time period as the end time point for the deflation procedure.

18. The sphygmomanometer according to claim 13, wherein the frequency detection circuit comprises:

a first frequency acquisition circuit configured to acquire a first frequency of the ultrasonic signal emitted by the ultrasonic wave transmission mechanism at a start time point of each time period;

a second frequency acquisition circuit configured to acquire a second frequency of the ultrasonic reflection signal received by the ultrasonic wave reception mechanism at an end time point of each time period; and a difference calculation circuit configured to calculate the difference in accordance with the second frequency and the first frequency.

19. The sphygmomanometer according to claim 17, wherein the frequency detection circuit comprises:

a first frequency acquisition circuit configured to acquire a first frequency of the ultrasonic signal emitted by the ultrasonic wave transmission mechanism at a start time point of each time period;

a second frequency acquisition circuit configured to acquire a second frequency of the ultrasonic reflection signal received by the ultrasonic wave reception mechanism at an end time point of each time period; and a difference calculation circuit configured to calculate the difference in accordance with the second frequency and the first frequency.

20. The sphygmomanometer according to claim 12, wherein the envelope is of a size matching a size of a finger or toe of a human body.

* * * * *